United States Patent [19]

Butterworth et al.

[11] 4,082,886
[45] Apr. 4, 1978

[54] LIQUID ABSORBENT FIBROUS MATERIAL AND METHOD OF MAKING THE SAME

[75] Inventors: George A. M. Butterworth, Western Springs; Robert T. Elias, Downers Grove, both of Ill.

[73] Assignee: Johnson & Johnson, New Brunswick, N.J.

[21] Appl. No.: 824,380

[22] Filed: Aug. 15, 1977

[51] Int. Cl.$^2$ .............................................. B32B 3/00
[52] U.S. Cl. ................... 428/284; 156/62.8; 156/181; 156/272; 156/306; 428/286; 428/288; 428/289; 428/296; 428/298; 428/299; 428/304; 428/535; 428/537; 428/913
[58] Field of Search .............. 156/62.2, 62.8, 181, 156/2.72, 306; 428/224, 284, 286, 288, 289, 296, 298, 304, 326, 535, 537, 227, 913

[56] References Cited
U.S. PATENT DOCUMENTS

| | | | |
|---|---|---|---|
| 2,624,079 | 1/1953 | Duvall | 428/299 |
| 2,798,283 | 7/1957 | Magat et al. | 428/401 |
| 3,917,448 | 11/1975 | Wood | 19/145.5 |
| 4,018,646 | 4/1977 | Ruffs | 428/297 |

*Primary Examiner*—James J. Bell

[57] ABSTRACT

The invention of the present application comprises a high loft, low density, nonwoven fibrous material and method of making the same. The material has good wet strength, softness, abrasion resistance, and liquid absorbency and retention, and is formed of a plurality of irregularly arranged, intersecting, overlapping, mechanically interengaged, loosely assembled fibers including both synthetic and natural wood pulp fibers which are present in different proportions in various regions parallel to the median plane of the material. Segments of said synthetic wood pulp fibers are heat fused with other segments of synthetic wood pulp fibers and with segments of other fibers at a plurality of junctures throughout the fibrous material to form a self-supporting fibrous structure which does not require any additional binder.

31 Claims, 3 Drawing Figures

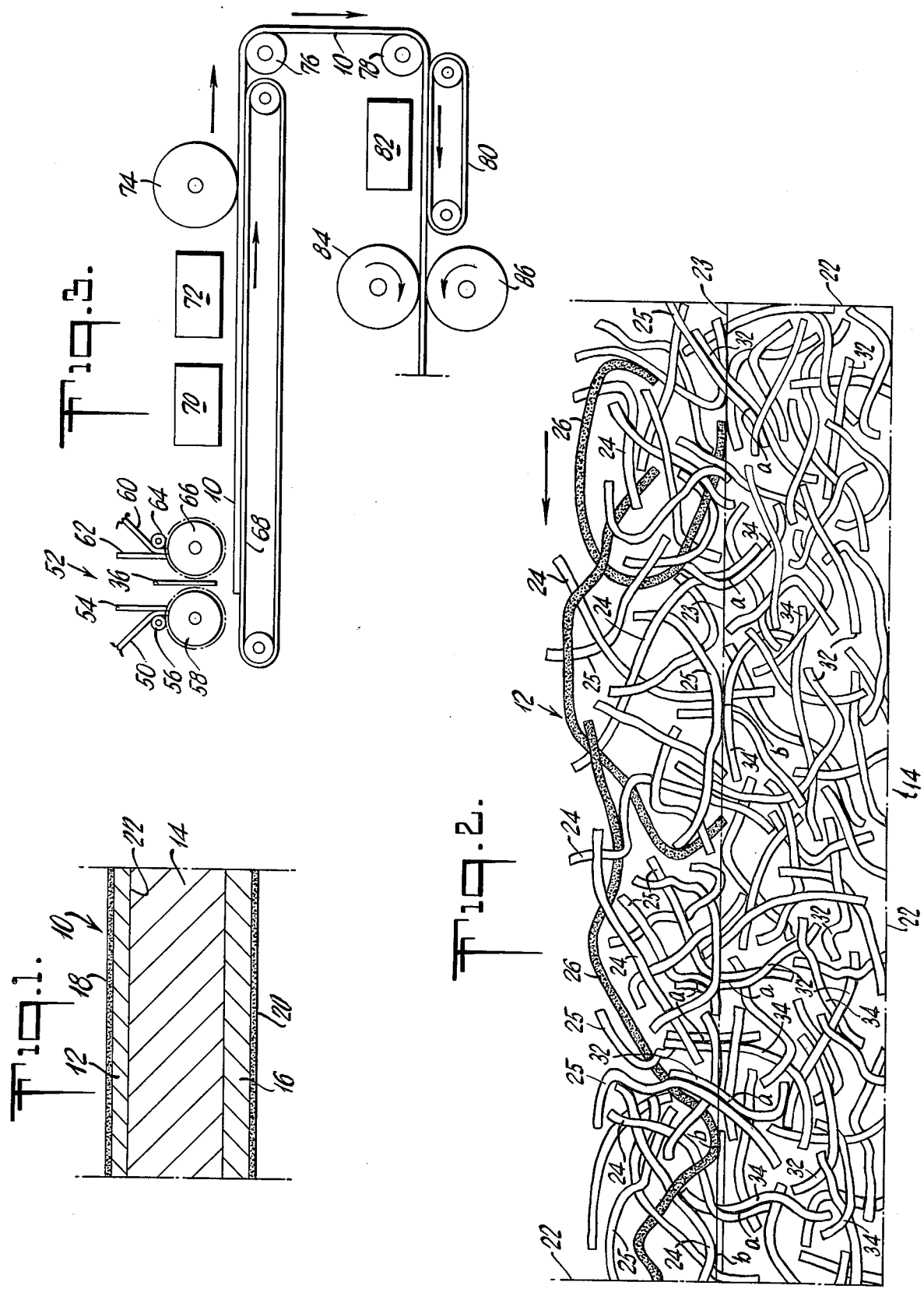

LIQUID ABSORBENT FIBROUS MATERIAL AND METHOD OF MAKING THE SAME

This application relates to a liquid absorbent, high loft, low density, non-woven fibrous material, such as an air-laid web or fabric, containing both natural wood pulp fibers and synthetic wood pulp fibers as two constitutents thereof, particularly a material in which said two types of fiber are present in different proportions in various regions parallel to the midplane thereof to provide good liquid absorbency and retention, and to a method of producing such a material.

BACKGROUND OF THE INVENTION

Synthetic polymeric fibers that have physical and morphological characteristics generally similar to pulp fibers produced from natural woods have been known for approximately 10 years. Examples of such fibers are the synthetic wood pulp fibers formed of polyethylene that are sold by Crown Zellerbach under the trademark SWP.

Various methods of making synthetic wood pulp fibers are known, including (1) solution polymerization accompanied by stirring, (2) dissolving a preformed polymer and subjecting the solution to an anti-solvent, or (3) forming the polymer at the interface between liquid layers, with localized stirring provided to pull the polymers thus formed into fibrillated forms. Examples of methods of producing synthetic wood pulp fibers are disclosed in U.S. Pat. Nos. 2,999,788, 2,708,617 and 2,798,283.

As used in this specification and the appended claims, the term "synthetic wood pulp fibers" means synthetic, water dispersible, thermoplastic, elongated, supple, randomly bent polymeric fibers are fibrils generally similar in size and shape to conventional wood pulp fibers produced from naturally occurring woods. Each such "synthetic wood pulp fiber" is of irregular cross sectional shape measured at any given point along its length, and in addition is non-uniform in cross section along its length. The predominant shape of the fibers is usually rather ribbon-like, in contrast to the hollow cylinders of natural wood pulp fibers.

The present invention utilizes synthetic wood pulp fibers in a high loft, low density, non-woven fibrous material such as an air-laid web or fabric. Non-woven materials are structures which consist of an assemblage or web of irregularly arranged fibers, joined randomly or more or less systematically by mechanical, chemical or other means.

These materials are well known in the art, having gained considerable prominence within the last twenty years or so in the consumer market, the industrial market, and the hospital field. For example, non-woven materials are becoming increasingly important in the textile and related fields, one reason being because of their low cost of manufacture for a given coverage as compared to the cost of more conventional textile fabrics made by weaving, knitting of felting. Typical of their use is the production of hospital caps, dental bibs, eye pads, dress shields, shoe liners, shoulder pads, skirts, hand towels, handkerchiefs, tapes, bags, table napkins, curtains, draperies, and the like.

Other applications for non-woven materials include wipes, scrubs, and other cleaning devices, as well as infants' diapers, surgical bandages, surgical sponges, sanitary napkins, disposable bed pads, and other absorbent products. Non-woven materials that possess the characteristics of high liquid absorption and high liquid retention are especially useful in all these latter applications.

A number of processes and types of apparatus are known for producing non-woven materials. These include (1) mechanical techniques (e.g. carding or garnetting), (2) wet laying techniques (e.g. inclined wire paper apparatus, cylinder paper apparatus, etc.), and (3) air-laying techniques. The high loft, low density, non-woven materials such as webs or fabrics to which this invention relates may suitably be produced, in the manner to be explained in detail below, from layers of material manufactured by well-known air-laying processes.

SUMMARY OF THE INVENTION

The present invention makes possible the production of high loft, low density, non-woven fibrous materials having the characteristics of high liquid absorption and high liquid retention, which are, as indicated above, desirable for many applications. The non-woven material of this invention also has good wet strength, softness and abrasion resistance.

The non-woven fibrous material of this invention comprises a plurality of irregularly arranged, intersecting, overlapping, mechanically interengaged, loosely assembled fibers including both natural wood pulp fibers and synthetic wood pulp fibers. These two types of fibers are present in different proportions in at least three different regions positioned parallel to the median plane of the material.

To produce a high level of liquid absorption in the product of this invention, it is necessary to have a facing region at one external boundary surface of the non-woven material that is not too water repellent to prevent a quantity of aqueous liquid from passing through that region into the main body of the material. On the other hand, a certain balance of wettability is required in the fibrous facing region, since it must have a lesser affinity for water than the interior region of the material, in order that liquid that has passed through the facing region from the outside will remain within the material rather than pass back out through the facing region. While providing this desired balance of wettability, the facing region must have an external boundary surface that also exhibits good softness and abrasion resistance.

Still different characteristics are required of the central region of the non-woven material, as well as the region adjacent the other external boundary surface of the material, in order to give the product of this invention a high level of liquid retention. Thus, the central portion of the material must constitute a reservoir region in which liquid can be stored once it has passed through the absorbent facing region. At the same time, the region of the material that defines the external boundary surface that lies opposite the facing region should provide good wet strength, softness and abrasion resistance, as well as provide an effective barrier to the passage of any substantial amount of aqueous liquid such as would defeat the desired property of high liquid retention by the material.

Surprisingly, it has been found that this balance of certain characteristics, and the contrasting of other characteristics depending upon the location within the non-woven material of this invention, can be achieved by incorporating different, controlled amounts of natural wood pulp fibers and synthetic wood pulp fibers in the three regions of the material just described. In the manufacture of the product of this invention, the desired proportions of natural and synthetic wood pulp fibers are first positioned in the indicated regions, and the fibrous assemblage is then subjected to heat without pressure to form a stable fibrous structure in which the three different regions exhibit different desired characteristics.

The first region of the non-woven material of this invention is the facing region, in which synthetic wood pulp fibers are present in an amount from about 6 percent to about 30 per cent by weight of the fibers. The second region is the absorbent reservoir region, in which synthetic wood pulp fibers are present in the range from about 4 percent to about 15 percent and in a smaller proportion than in the first region. The third region is a capillary distribution network region, in which synthetic wood pulp fibers are present in the range from about 5 percent to about 20 percent and in a proportion greater than the proportion of such fibers in the second region but less than in the first region.

The first and third regions just described are located on opposite sides of the second region. The melting point of the synthetic wood pulp fibers in the non-woven material of this invention is lower than the melting point of all other fibers in the material. Segments of the synthetic wood pulp fibers in the material are heat fused with other segments of synthetic wood pulp fibers and with segments of still other fibers, at a plurality of junctures throughout the material, to form a selfsupporting fibrous structure in the absence of any additional binder.

Improved results are obtained if the amount of synthetic wood pulp fibers in the first facing region is from about 15 percent to about 25 percent by weight of the fibers, the amount in the second absorbent reservoir region is about 8 per cent to about 12 percent by weight, and the amount in the third capillary distribution network region is about 10 percent to about 18 percent. The preferred percentages of synthetic wood pulp fibers in the first, second and third regions, respectively, are about 20 percent, 10 percent and 15 percent by weight of the fibers in the region in question.

The effect of the synthetic wood pulp fibers in the various regions of the non-woven material of this invention will depend on whether they are formed of a non-wettable material and whether they are coated, as are certain commercial forms of such fibers, with a surfactant.

It is preferred that the fibers of all types in the first region constitute about 10 percent of the total weight of the material, the fibers of all types in the second region about 70 percent, and the fibers of all types in the third region about 20 percent of that total weight. Best results are obtained when the first facing region also includes about 5 to about 15 percent by weight of textile length fibers, and the exposed boundary surface portions of the first region contain about 20 to about 30 percent by weight of synthetic wood pulp fibers. It is also preferred that the exposed boundary surface portions of the first facing region include about 1 percent by weight of adhesive binder, and that the exposed boundary surface of the first region be partially smoothed by light calendering. Still better results are obtained if the exposed boundary surface of the third capillary distribution network region comprises interengaged fibers, some of which are connected with one another through hydrogen bonding and others of which are connected through heat fused junctures of synthetic wood pulp fibers with each other and also with other fibers of said region, to form a porous, paper-like layer of compacted and densified coherent fibers having high capillarity and fluid retentivity.

The method of this invention comprises bringing together at least three layers of fibers in the proportions described above and applying heat in the absence of pressure to the plurality of fibers making up the various layers of regions, to fuse and bond at least some of the synthetic wood pulp fibers with other fibers to form a self-supporting fiber structure in the absence of any additional binder. Apparatus is disclosed below to produce one form of the absorbent fibrous material of this invention in which the disposition and arrangement of the fibers is substantially the same in all directions across the surface of the material and substantially uniform from one exposed boundary surface to the other, regardless of the relative portions of natural wood pulp fibers and synthetic wood pulp fibers in particular regions of the material. The material of this invention may also comprise irregularly arranged, loosely assembled fibers that define interstices between the fibers, fibers in at least one of each pair of contiguous regions extending as bridging fibers across the interface between the contiguous regions, with only outer end portions of the bridging fibers positioned within interstices between fibers in the other region of the pair and in heat fused contact with fibers in that other region.

BRIEF DESCRIPTION OF THE DRAWING

The invention will now be described with reference to the accompanying drawing, in which:

FIG. 1 is an enlarged, fragmentary, diagrammatic representation in cross-section of the absorbent fibrous material of this invention;

FIG. 2 is a still further enlarged, fragmentary, diagrammatic representation in cross-section of a portion of another embodiment of the fibrous material of this invention; and FIG. 3 is a diagrammatic side elevation view of one form of apparatus for producing the fibrous material of FIG. 1.

DETAILED DESCRIPTION OF THIS INVENTION

Over-all Structure of Product

The product of this invention is a high loft, low density, non-woven fibrous material having good wet strength, softness, abrasion resistance, and liquid absorbency and retention. The material comprises a plurality of irregularly arranged, intersecting, overlapping, mechanically interengaged, loosely assembled fibers including both natural wood pulp fibers and synthetic wood pulp fibers. The two types of fibers are present in different proportions in various regions positioned parallel to the median plane of the material.

As indicated in FIG. 1, non-woven fibrous material 10 is comprised of fibers arranged as described above in facing region 12, absorbent reservoir region 14, and capillary distribution network region 16. Regions 12 and 16 are contiguous with region 14 and lie on opposite sides thereof.

It is preferred that the fibers of all types contained in the first or facing region of the non-woven material of this invention constitute about 10 percent of the total weight of the material. The fibers of all types in the second reservoir region should constitute about 70 percent of the total weight of the material, in order to provide the largest practicable space in which to store retained liquid. For best results, the fibers of all types in the third or capillary distribution network region should make up the remainder of the material, or in other words, about 20 percent of the total weight of the material.

The melting point of the synthetic wood pulp fibers in fibrous material 10 is lower than the melting point of all other fibers in the material.

With synthetic wood pulp fibers distributed throughout all three regions of the absorbent material of this invention, a plurality of contacts of synthetic wood pulp fibers with each other and with the other fibers of the material are present from one external surface other material to the other. At at least some of these contact points, segments of synthetic wood pulp fibers are heat fused with other segments of synthetic wood pulp fibers or with segments of other fibers, to form a self-supporting fibrous structure in the absence of any additional binder.

Facing Region

Facing region 12 includes both natural wood pulp fibers and synthetic wood pulp fibers, all of which are less than one-quarter inch in length. For fabric strength, facing region 12 may if desired also contain about 5 to 15 percent by weight of textile length fibers, which are longer than one-quarter inch and are typically one-half to 1½ inch or longer in length.

The desired characteristics of facing region 12 are obtained when synthetic wood pulp fibers are present in an amount from about 6 percent to about 30 percent by weight of all the fibers present in the region. Improved results are obtained if synthetic wood pulp fibers are present in the region in an amount from about 15 percent to about 25 percent by weight of the fibers, and it is preferred to have synthetic wood pulp fibers present in the facing region in an amount about 20 percent by weight.

The wet strength and abrasion resistance of absorbent fibrous material 10 are improved if exposed boundary surface portions 18 of facing region 12 contain about 20 to about 30 percent by weight of synthetic wood pulp fibers. In such case, the remainder of region 12 may contain about 6 percent to about 30 percent by weight of synthetic wood pulp fibers. It is also preferred for surface portion 18 of facing region 10 to include about 1 percent by weight of adhesive binder. Still further improvement is obtained if the exposed boundary surface defined by surface portions 18 is partially smoothed by light calendering throughout the area of the surface.

As stated above, it is preferred that the fibers of all types contained in the first or facing region of the nonwoven material of this invention constitute about 10 percent of the total weight of the material. A facing region of this thickness will provide a stable external boundary surface, and at the same time provide a fibrous structure that will permit ready passage of aqueous liquid into the central portions of the material of this invention and help retain it there once absorbed. It will also help augment the overall strength of the fibrous material, as well as the liquid retention capacity of the material.

Absorbent Reservoir Region

Second absorbent reservoir region 14, like first facing region 12, includes both natural wood pulp fibers and synthetic wood pulp fibers. Ordinarily, no other types of fibers are included in this region.

As in the rest of fibrous non-woven material 10, the melting point of the synthetic wood pulp fibers in region 14 is lower than the melting point of the other fibers in the region. Segments of synthetic wood pulp fibers are heat fused with other segments of synthetic wood pulp fibers and with segments of natural wood pulp fibers, to form a self-supporting fibrous structure in the absence of any additional binder.

Synthetic wood pulp fibers are present in absorbent reservoir region 14 in a smaller proportion than the proportion of synthetic wood pulp fibers in first region 12. A satisfactory absorbent reservoir is provided when synthetic wood pulp fibers are present in region 14 in an amount from about 4 per cent to about 15 percent by weight of the fibers in the region. Improved results are obtained when synthetic wood pulp fibers are present in the second region in an amount from about 8 per cent to about 12 percent by weight of the fibers, and it is preferred that they be present in an amount about 10 percent by weight.

Capillary Distribution Region

Third region 16 of fibrous material 10, which provides a capillary distribution network, contains both natural wood pulp fibers and synthetic wood pulp fibers, and usually no other types of fibers. Synthetic wood pulp fibers are present in this region in a proportion greater than the proportion of synthetic wood pulp fibers in second region 14, but less than the proportion in first region 12.

Satisfactory results are obtained when the synthetic wood pulp fibers present in third region 16 constitute about 5 percent to about 20 percent by weight of the fibers in that region. Improved results are obtained when synthetic wood pulp fibers in that region constitute about 10 percent to about 18 percent by weight, and it is preferred that they constitute about 15 percent by weight of the fibers in the third region. Still further improvement is obtained if exposed boundary surface portions 20 of third region 16 contain about 20 to about 30 per cent by weight of synthetic wood pulp fibers, while the remainder of region 16 contains from about 10 to about 18 percent of synthetic wood pulp fibers.

The effectiveness of capillary distribution network region 16 can be increased if exposed boundary surface 20 comprises interengaged fibers some of which are connected with one another through hydrogen bonding, and others through heat fused junctures of synthetic wood pulp fibers with each other and also with other fibers in the region, to form a porous, paper-like layer of compacted and densified coherent fibers having high capillarity and retentivity, of the general type disclosed in U.S. Pat. No. 2,955,641 to Burgeni. p With respect to FIG. 1, it should be pointed out that while for purposes of clarity this figure shows fibrous layers and regions 12 through 20 adjoining each other at sharply defined interfaces, this is only a diagrammatic showing. In the actual product of this invention is a more or less gradual transition from one fibrous layer or region to another, with fibers intermingled with each other while each layer or region merges into the adjoining one.

Disposition of Fibers

Fibrous material 10 shown in FIG. 1 may, if desired, be formed by means of an air deposition process, in which the fibers of regions 12 through 20 are all laid down simultaneously. In such case, the disposition and arrangement of the loosely assembled fibers making up fibrous material 10 is substantially the same in all directions across the surface of the material, and substantially uniform from one exposed boundary surface 18 to the other boundary surface 20 without regard to the relative proportions of natural wood pulp fibers and synthetic wood pulp fibers in various regions of the material.

Fibrous material 10 may also be produced by bringing together as separate, self-supporting layers of fibers the irregularly arranged fibers that will make up the respective fibrous regions of material 10 parallel to the median plane thereof. In this case, fibers of at least one of each pair of regions 10 through 20 that are located contiguous to each other extend as bridging fibers across the interface between the contiguous regions. Only the outer end portions of these bridging fibers lie within the interstices between the fibers in the other region of the pair. At least some of them there contact and are fused with segments of fibers lying in the other region.

FIG. 2 is a fragmentary, enlarged, diagrammatic drawing in cross-section of a portion of region 12 and a portion of region 14 (outlined by dashed lines 22) on either side of interface 23 between the two regions. In FIG. 2, region 12 contains shorter fibers 24, 25 and longer textile fibers 26 (stippled in the Figure) intermingled therewith. Shorter fibers 24 are natural wood pulp fibers and shorter fibers 25 are synthetic wood pulp fibers. The upper portion of region 14 shown in FIG. 2 includes only natural wood pulp fibers 32 and synthetic wood pulp fibers 34.

The bonding of fibers in regions 12 and 14 shown in FIG. 2 is similar to that disclosed in commonly assigned copending application for patent filed simultaneously herewith by George A. M. Butterworth, Robert T. Elias and Wayne D. Miller, entitled "Fibrous Material and Method of Making the Same." As is seen from FIG. 2, the greater part of the fibrous mass that comprises regions 12 and 14 of fibrous material 10 lies within the interior of the fibrous structure of the respective region as a whole. However, some fibers 24 and 25 of region 12 have free fiber ends extending downwardly from the plane which is the effective lower boundary surface of region 12 at interface 23. Some fibers 32 and 34 of region 14 likewise have free fiber ends extending upwardly from the plane of the upper boundary surface of that region. At least some of these free fiber ends are inserted in the interstices between the fibers of the other layer.

The resulting interfiber contact and fusion bonding in both region 12 and region 14 between fiber segments, at least some of which are synthetic wood pulp fibers, is illustrated in FIG. 2 in diagrammatic fashion. FIG. 2 is not intended to suggest that the precise types of contact shown there are necessarily identifiable in the product of this invention, but it is intended to suggest that there is some considerable degree of contact and heat fusion bonding between the fibers in question.

As is seen from FIG. 2, areas of contact between some exposed fiber end portions of synthetic wood pulp fibers 25 and 34, respectively, with other fiber segments, which may or may not be synthetic wood pulp fibers, are indicated at several locations designated by the letter "a" in the Figure. Heat fusion bonding between synthetic wood pulp fiber segments and other fibers is also indicated at these locations. Still another type of fiber contact and heat fusion bonding is indicated by the letter "b" in FIG. 2, with essentially two-dimensional contact of parallel fiber segments, at least one of which is a synthetic wood pulp fiber segment, lying at the respective boundary surfaces of fibrous regions 12 and 14.

Degree of Wettability of Various Regions

The degree of wettability of facing region 12, absorbent reservoir region 14, and capillary distribution network region 16, respectively, depends not only on the proportion of synthetic wood pulp fibers present but upon whether these fibers are wettable or non-wettable. Non-wettable synthetic wood pulp fibers are formed of hydrophobic polymers, and in commercial form should be free of any surfactant film on the external surface of the fibers. A surfactant film on the fibers of course increases the wettability of the fibers.

In the preferred form of the absorbent, non-woven material of this invention, the desired balance of wettability of facing region 12 is achieved through inclusion of relatively non-wettable synthetic wood pulp fibers. Region 16, lying at the opposite surface of the material, preferably includes synthetic wood pulp fibers that are highly non-wettable.

In contrast to regions 12 and 16, absorbent reservoir region 14 preferably includes synthetic wood pulp fibers that are as wettable as possible. These fibers may be, for example, synthetic wood pulp fibers of a type commercially available that are coated with a surfactant film and are thus rendered wettable by an aqueous medium.

METHOD OF THIS INVENTION

In the method of this invention, a plurality of irregularly arranged, intersecting, overlapping, mechanically interengaged, loosely assembled fibers, including both natural wood pulp fibers and synthetic wood pulp fibers, is brought together to position the two types of fibers in different proportions in the various regions described above in connection with the description of the product of this invention. Heat is then applied in the absence of pressure to the plurality of fibers thus arranged, to fuse and bond at least some of the synthetic wood pulp fibers with other segments of fibers at a plurality of junctures throughout the fibrous material. A fiber structure that is self-supporting in the absence of any additional binder is thus produced.

As indicated above, fibrous material 10 shown in FIG. 1 may if desired be formed by means of an air deposition process. FIG. 3 provides a diagrammatic drawing in side elevation of apparatus that may be used in this manner.

The left hand portion of the apparatus shown in FIG. 3 is similar to the web forming apparatus disclosed in commonly assigned U.S. Pat. Nos. 3,740,797 to Farrington, 3,768,118 to Ruffo et al., and 3,772,739 to Lovgren. A board 50 of synthetic wood pulp fibers is fed into air deposition apparatus 52 between guide plate 54 and feed roll 56, into edgewise contact with lickerin 58, which separates the web into individual fibers of synthetic wood pulp. At the same time, a board 60 of natural wood pulp fibers is fed into air deposition apparatus 52 between guide plate 62 and feed roll 64, into edgewise contact with lickerin 66, which separates the web into individual fibers of natural wood pulp.

As synthetic wood pulp fibers and natural wood pulp fibers are directed downward from lickerins 58 and 66, respectively, they are intermingled to form fibrous material 10, which moves from left to right with the endless belt in FIG. 3. Air deposition apparatus 52 can be adjusted, as explained in the patents referred to above which disclose such apparatus, to produce different proportions of synthetic wood pulp fibers and other fibers in the various regions of the resulting non-woven fibrous material at or parallel to the median plane of the material.

For additional fabric strength, if desired, adhesive binder in latex form may be sprayed on the exposed boundary surface portions 18 of region 12 of the resulting fibrous material 10. If added, the binder should be applied in an amount equivalent to about 1 percent by dry weight of the resulting fibrous material. Any suitable binder employed with non-woven fibrous materials may be used. Binder applying means 70 is shown diagrammatically in FIG. 3, and drying means 72, such as a dielectric heater, infra-red heater, radiant heater, or other heating means, is shown diagrammatically at 72.

As a subsequent step in the method of this invention, exposed boundary surface 18 of region 12 of fibrous material 10 can be lightly calendered to partially smooth the boundary surface. Calendering means 74 is shown diagrammatically in FIG. 3.

In a preferred form of the method of this invention, fibrous material 10 is led around guide rolls 76 and 78 onto the upper reach of endless belt 80, which is moving from right to left in FIG. 3. Water is sprayed lightly on material 10 from spray means 82 shown diagrammatically, and heat and pressure are then applied to exposed boundary surfaces 20 of region 16 at heated roller 84 and back-up roller 86. The application of heat and pressure to the slightly wet, exposed boundary surface of capillary distribution network region 16 melts synthetic wood pulp fibers and also produces hydrogen bonding between segments of natural wood pulp fibers, to create a micro-capillary network at that surface and form a porous, paper-like layer of compacted and densified coherent fibers having high capillarity and fluid retentivity. The layer thus described is similar to the porous paper-like layer disclosed and claimed in U.S. Pat. No. 2,955,641 to Burgeni.

The product resulting from use of the method described is a high loft, low density, non-woven fibrous material having good wet strength, softness, abrasion resistance, and good liquid absorbency and liquid retention.

The above detailed description is given for clearness of understanding only. No unnecessary limitations should be understood therefrom, as modifications will be obvious to those skilled in the art.

What is claimed is:

1. A high loft, low density, nonwoven fibrous material having good wet strength, softness, abrasion resistance, and liquid absorbency and retention which comprises a plurality of irregularly arranged, intersecting, overlapping, mechanically interengaged, loosely assembled fibers including both natural wood pulp fibers and synthetic wood pulp fibers, said two types of fibers being present in different proportions in various regions positioned parallel to the median plane of the material, said regions including a first facing region in which synthetic wood pulp fibers are present in an amount from about 6 percent to about 30 percent by weight of the fibers, a second absorbent reservoir region in which synthetic wood pulp fibers are present in a smaller proportion than the proportion of synthetic wood pulp fibers in said first region, and a third capillary distribution network region in which synthetic wood pulp fibers are present in a proportion greater than the proportion of synthetic wood pulp fibers in said second region but less than the proportion of synthetic wood pulp fibers in said first region, said first and third regions being located on opposite sides of said second region, the melting point of said synthetic wood pulp fibers being lower than the melting point of all other fibers in said fibrous material, segments of said synthetic wood pulp fibers being heat fused with other segments of synthetic wood pulp fibers and with segments of other fibers at a plurality of junctures throughout said fibrous material to form a self-supporting fibrous structure which does not require any additional binder.

2. The absorbent fibrous material of claim 1 in which synthetic wood pulp fibers are present in said second absorbent reservoir region in an amount from about 4 percent to about 15 percent by weight of the fibers.

3. The absorbent fibrous material of claim 1 in which synthetic wood pulp fibers are present in said third capillary distribution network region in an amount from about 5 percent to about 20 percent by weight of the fibers.

4. The absorbent fibrous material of claim 1 in which synthetic wood pulp fibers are present in said first facing region in an amount from about 15 percent to about 25 percent by weight of the fibers, in said second absorbent reservoir region in an amount from about 8 percent to about 12 percent by weight of the fibers, and in said third capillary distribution network region in an amount from about 10 percent to about 18 percent by weight of the fibers.

5. The absorbent fibrous material of claim 1 in which synthetic wood pulp fibers constitute about 20 percent by weight of the fibers in said first facing region, about 10 percent by weight of the fibers in said second absorbent reservoir region, and about 15 percent by weight of the fibers in said third capillary distribution network region.

6. The absorbent fibrous material of claim 1 in which said first facing region includes about 5 to about 15 percent by weight of textile length fibers.

7. The absorbent fibrous material of claim 1 in which the exposed boundary surface portions of said first facing region contain about 20 to about 30 percent by weight of synthetic wood pulp fibers and the remainder of said region contains from about 6 percent to about 30 percent by weight of synthetic wood pulp fibers.

8. The absorbent fibrous material of claim 1 in which the exposed boundary surface portions of said first facing region include about 1 percent by weight of adhesive binder.

9. The absorbent fibrous material of claim 1 in which the exposed boundary surface of said first facing region is partially smoothed by light calendering throughout said surface.

10. The absorbent fibrous material of claim 1 in which the exposed boundary surface of said third capillary distribution network region comprises interengaged fibers some of which are connected with one another through hydrogen bonding, and others through heat fused junctures of synthetic wood pulp fibers with each other and also with other fibers of said region, to form a porous, paper-like layer of compacted and densified coherent fibers having high capillarity and fluid retentivity.

11. The absorbent fibrous material of claim 1 in which the exposed boundary surface portions of said third capillary distribution network region contain about 20 to about 30 percent by weight of synthetic wood pulp fibers, and the remainder of said region contains from about 10 percent to about 18 percent by weight of synthetic wood pulp fibers.

12. The absorbent fibrous material of claim 1 in which the fibers of all types in said first facing region constitute about 10 percent of the total weight of said material, the fibers of all types in said second absorbent reservoir region constitute about 70 percent of the total weight of said material, and the fibers of all types in said third capillary distribution network region constitute about 20 percent of the total weight of the material.

13. The absorbent fibrous material of claim 1 in which said irregularly arranged, loosely assembled fibers define interstices therebetween and in which fibers of at least one of each pair of said regions that are located contiguous to each other extend as bridging fibers across the interface between said contiguous regions with only outer end portions of said bridging fibers positioned within interstices between fibers in the other region of the pair, where they contact and are fused with segments of fibers lying in said other region.

14. The absorbent fibrous material of claim 1 in which the disposition and arrangement of said loosely assembled fibers is substantially the same in all directions across the surface of the material and substantially uniform from one exposed boundary surface of the material to the other without regard to the relative proportions of natural wood pulp fibers and synthetic wood pulp fibers in particular regions of said material.

15. A high loft, low density, nonwoven fibrous material having good wet strength, softness, abrasion resistance and liquid absorbency and retention which comprises a plurality of irregularly arranged, intersecting, overlapping, mechanically interengaged, loosely assembled fibers including both natural wood pulp fibers and synthetic wood pulp fibers, said two types of fibers being present in different proportions in various regions positioned parallel to the median plane of the material, said regions including a first facing region containing about 20 percent by weight of synthetic wood pulp fibers and about 10 percent by weight of textile length fibers, a second absorbent reservoir region in which synthetic wood pulp fibers constitute about 10 percent by weight of the fibers, and a third capillary distribution network region in which synthetic wood pulp fibers constitute about 15 percent by weight of the fibers, the fibers in said first facing region constituting about 10 percent of the total weight of the material, and fibers in said second absorbent reservoir region constituting about 70 percent of the total weight of the fibers of the material, and the fibers in the third capillary distribution network region constituting about 20 percent of the total weight of the material, said first and third regions being located on opposite sides of said second region, the melting point of said synthetic wood pulp fibers being lower than the melting point of all other fibers in said fibrous material, segments of said synthetic wood pulp fibers being heat fused with other segments of synthetic wood pulp fibers and with segments of other fibers at a plurality of junctures throughout said fibrous material to form a self-supporting fiber structure in the absence of any additional binder, the exposed boundary surface of said first facing region being partially smoothed by light calendering throughout said surface, and the exposed boundary surface of said third capillary distribution network region comprising interengaged fibers some of which are connected with one another through hydrogen bonding, and others through heat fused junctures of synthetic wood pulp fibers with each other and also with other fibers of said region, to form a porous, paper-like layer of compacted and densified coherent fibers having high capillarity and fluid retentivity.

16. A method of producing a high loft, low density, nonwoven fibrous material having good wet strength, softness, abrasion resistance, and liquid absorbency and retention which comprises:
  bringing together a plurality of irregularly arranged, intersecting, overlapping, mechanically interengaged, loosely assembled fibers including both natural wood pulp fibers and synthetic wood pulp fibers to position said two types of fibers in different proportions in various regions parallel to the median plane of the material, with synthetic wood pulp fibers being positioned in a first facing region in an amount from about 6 percent to about 30 percent by weight of the fibers, in a second absorbent reservoir region in a smaller proportion than in said first region, and in a third capillary distribution network region in a proportion greater than in said second region but less than in said first region, said first and third regions being located on opposite sides of said second region, the melting point of said synthetic wood pulp fibers being lower than the melting point of all other fibers in said fibrous material; and
  applying heat in the absence of pressure to said plurality of fibers thus arranged to fuse and bond at least some of said synthetic wood pulp fibers with other segments of synthetic wood pulp fibers and with segments of other fibers at a plurality of junctures throughout said fibrous material to form a selfsupporting fiber structure which does not require any additional binder.

17. The method of claim 16 in which synthetic wood pulp fibers are positioned in said second absorbent reservoir region in an amount from about 4 percent to about 15 percent by weight of the fibers.

18. The method of claim 16 in which synthetic wood pulp fibers ae positioned in said third capillary distribution region in an amount from about 5 percent to about 20 percent by weight of the fibers.

19. The method of claim 16 in which the fibers positioned in said first facing region constitute about 10 percent of the total weight of fibers in said material, the fibers positioned in said second absorbent reservoir region constitute about 70 percent of the total weight of fibers in said material, and the fibers positioned in said third capillary distribution network region constitute about 20 percent of the total weight of the fibers of the material.

20. The method of claim 16 in which synthetic wood pulp fibers are positioned in said first facing region in an amount from about 15 percent to about 25 percent by weight of the fibers, in said second absorbent reservoir region in an amount from about 8 percent to about 12 percent by weight of the fibers, and in said third capillary distribution network region in an amount from about 10 percent to about 18 percent by weight of the fibers.

21. The method of claim 16 in which synthetic wood pulp fibers are positioned in said first facing region in an amount about 20 percent by weight of the fibers, in said second absorbent reservoir region in an amount about 10 percent by weight of the fibers, and in said third capillary distribution network region in an amount about 15 percent by weight of the fibers.

22. The method of claim 16 in which textile length fibers are positioned in said first facing region in an amount from about 5 to about 15 percent by weight of the fibers.

23. The method of claim 16 in which about 20 to about 30 percent by weight of synthetic wood pulp fibers are positioned in the exposed boundary surface portions of said first facing region, and about 6 percent to about 30 percent by weight of synthetic wood pulp fibers are positioned in the remainder of said region.

24. The method of claim 16 which includes a subsequent step of spraying adhesive binder in latex form on the exposed boundary surface portions of said first facing region in an amount equivalent to about 1 percent by dry weight of binder.

25. The method of claim 16 which includes the step of lightly calendering the exposed boundary surface of said first facing region of fibers in said absorbent fibrous material to partially smooth said boundary surface.

26. The method of claim 16 which includes the step of applying heat and pressure to the exposed boundary surfaces of said third capillary distribution network region to melt synthetic wood pulp fibers and create a micro-capillary network at said boundary surface, to form a porous, paper-like layer of compacted and densified coherent fibers having high capillarity and fluid retentivity.

27. The method of claim 26 in which said exposed boundary surface of said third capillary distribution network region is lightly sprayed with water immediately prior to applying heat and pressure as there specified.

28. The method of claim 16 in which synthetic wood pulp fibers are positioned in the exposed boundary surface portions of said third capillary distribution network region in an amount from about 20 to about 30 percent by weight of the fibers, and synthetic wood pulp fibers are positioned in the remainder of said third region in an amount from about 10 percent to about 20 percent by weight.

29. The method of claim 16 in which the fibers positioned in said three regions are brought together as discrete groups of fibers in respective layers in which the fibers are irregularly arranged to define interstices therebetween and to provide free fiber ends extending outwardly from the boundary surfaces of the layer, and when said three layers of fibers are brought together at least some of the fiber segments of synthetic wood pulp fibers of a given layer are brought into contact with the fibers of an adjacent layer of fibers by inserting only the outer end portions of at least some of the free fiber ends from said given layer into the interstices between fibers in said adjacent layer.

30. The method of claim 16 in which said loosely assembled fibers are positioned so as to be disposed in substantially the same general manner in all directions across the surface of the material and in a substantially uniform manner from one exposed boundary surface of the material to the other without regard to the relative proportions of natural wood pulp fibers and synthetic wood pulp fibers in particular regions of said material.

31. A method of producing a high loft, low density, nonwoven fibrous material having good wet strength, softness, abrasion resistance, and liquid absorbency and retention which comprises:

bringing together a plurality of irregularly arranged, intersecting, overlapping, mechanically interengaged, loosely assembled fibers including both natural wood pulp fibers and synthetic wood pulp fibers to position said two types of fibers in different proportions in various regions parallel to the median plane of the material, the synthetic wood pulp fibers being positioned in a first facing region in an amount equal to about 20 percent by weight of the fibers, in a second absorbent reservoir region in an amount equal to about 10 percent by weight of the fibers and in a third capillary distribution network region in an amount equal to about 15 percent by weight of the fibers, the fibers thus positioned in said first facing region constituting about 10 percent of the total weight of the material, the fibers positioned in said second absorbent reservoir region constituting about 70 percent of the total weight of the fibers of the material, and the fibers positioned in the third capillary distribution network region constituting about 20 percent of the total weight of the material, said first and third regions being located on opposite sides of said second region, the melting point of said synthetic wood pulp fibers being lower than the melting point of all other fibers in said fibrous material;

applying heat in the absence of pressure to said plurality of fibers thus arranged to fuse and bond at least some of said synthetic wood pulp fibers with other segments of synthetic wood pulp fibers and with segments of other fibers at a plurality of junctures throughout said fibrous material to form a self-supporting fiber structure which does not require any additional binder;

lightly calendering the exposed boundary surface of said first facing region to partially smooth said surface; and applying heat and pressure to the exposed boundary surface of said third capillary distribution network region to melt synthetic wood pulp fibers and create a micro-capillary network at said boundary surface, to form a porous, paper-like layer of compacted and densified coherent fibers having high capillarity and fluid retentivity.

* * * * *

UNITED STATES PATENT AND TRADEMARK OFFICE
CERTIFICATE OF CORRECTION

PATENT NO. : 4,082,886
DATED : April 4,1978
INVENTOR(S) : George A. M. Butterworth; Robert T. Elias It is certified that error appears in the above-identified patent and that said Letters Patent are hereby corrected as shown below:

```
In the References cited, "Ruffs" should be -- Ruffo --.
At Column 1, Line 36, "are" should be -- or --.
At Column 1, Line 60, "of" (first occurrence) should be --or --.
At Column 3, Line 30, "selfsupporting" should be
                -- self-supporting --.
At Column 3, Line 34, "facting" should be -- facing --.
At Column 4, Line 10, "of" should be -- or --.
At Column 5, Line 14, "absorbent material" should be --
                absorbent fibrous material --.
At Column 5, Line 15, "other" should be -- of the --.
At Column 6, Line 60, "Burgeni p" should be -- Burgeni.--.
At Column 6, Line 60, after "Burgeni." begin a new paragraph.
At Column 6, Line65, "invention is" should be -- invention
                there is --.
At Column 9, Line 37, "at" should be -- by --.
At Column 12, Line 43, "selfsupporting" should be -- self-
                supporting --.
At Column 12, Line 50, "ae" should be -- are --.
```

Signed and Sealed this

Thirty-first Day of October 1978

[SEAL]

Attest:

RUTH C. MASON
Attesting Officer

DONALD W. BANNER
Commissioner of Patents and Trademarks